United States Patent
Shi et al.

(10) Patent No.: US 12,331,047 B2
(45) Date of Patent: Jun. 17, 2025

(54) SYNTHESIS FOR 3-BROMO-5-(2-ETHYLIMIDAZO[1,2-ALPHA]PYRIDINE-3-CARBONYL)-2-HYDROXYBENZONITRILE

(71) Applicant: Atom Therapeutics Co., Ltd, Hangzhou (CN)

(72) Inventors: Dongfang Shi, Fremont, CA (US); Changjin Fu, Suzhou (CN); Jie Gu, Suzhou (CN); Min Zhang, Suzhou (CN); Weiwei Gong, Suzhou (CN); Pengfei Li, Suzhou (CN)

(73) Assignee: Atom Therapeutics Co., Ltd, Hangzhou (CN)

( * ) Notice: Subject to any disclaimer, the term of this patent is extended or adjusted under 35 U.S.C. 154(b) by 871 days.

(21) Appl. No.: 17/310,123

(22) PCT Filed: Jan. 17, 2020

(86) PCT No.: PCT/CN2020/072582
§ 371 (c)(1),
(2) Date: Jul. 18, 2021

(87) PCT Pub. No.: WO2020/147803
PCT Pub. Date: Jul. 23, 2020

(65) Prior Publication Data
US 2022/0041593 A1   Feb. 10, 2022

(30) Foreign Application Priority Data

Jan. 19, 2019 (CN) .......................... 201910057056.3
Jan. 14, 2020 (CN) .......................... 202010037085.6

(51) Int. Cl.
*C07D 471/04* (2006.01)

(52) U.S. Cl.
CPC .................................. *C07D 471/04* (2013.01)

(58) Field of Classification Search
CPC ..................................................... C07D 471/04
USPC ......................................................... 546/121
See application file for complete search history.

(56) References Cited

FOREIGN PATENT DOCUMENTS

WO      2018/090921      *   5/2018

* cited by examiner

*Primary Examiner* — Taofiq A Solola
(74) *Attorney, Agent, or Firm* — CBM PATENT CONSULTING, LLC

(57) ABSTRACT

A method for synthesizing 3-bromo-5-(2-ethylimidazo[1,2-a] pyridine-3-carbonyl)-2-hydroxybenzonitrile, particularly relates to a method for synthesizing a compound represented by a formula (III), and particularly relates to step A or step B; step A: a compound represented by a formula (I) and a compound represented by a formula (II) are first heated in an organic solvent to react, and the resulting reaction product and a base are heated in the presence of water to continue the reaction to obtain a compound represented by a formula (III); and step B: a compound represented by the formula (I), a compound represented by a formula (II), and a base are heated in an organic solvent to react, and the resulting reaction product is heated in the presence of water to continue the reaction to obtain a compound represented by a formula (III).

6 Claims, No Drawings

SYNTHESIS FOR 3-BROMO-5-(2-ETHYLIMIDAZO[1,2-ALPHA]PYRIDINE-3-CARBONYL)-2-HYDROXYBENZONITRILE

TECHNICAL FIELD

The invention belongs to the field of medicinal chemistry, and in particular, relates to a method for synthesizing the compound 3-bromo-5-(2-ethylimidazo[1,2-α]pyridine-3-carbonyl)-2-hydroxybenzonitrile.

BACKGROUND

Gout is a chronic metabolic disease caused by hyperuricemia resulted in purine metabolism disorder and/or uric acid excretion disorder in the human body, with a main feature of severe pain caused by the deposition of urate in joints and other parts. When the serum uric acid level in the body exceeds 6.8 mg/dL, monosodium urate crystals will deposit in the synovial fluid of human tissues, the cartilage of peripheral joints, the pinna of the ears, and the olecranon sac of the elbows. When such symptoms occur, it can be diagnosed as gout. URAT1 plays an important role in the reabsorption of uric acid from the cell to the lumen of the renal tubules, which is a main uric acid reabsorption protein in the human body and controls more than 90% of the reabsorption of uric acid after glomerular filtration. Therefore, inhibiting the transport of URAT1 can reduce the reabsorption of uric acid, promote the excretion of uric acid in the kidney, and achieve the effect of reducing the blood uric acid level in the body. 3-bromo-5-(2-ethylimidazo[1,2-α]pyridine-3-carbonyl)-2-hydroxybenzonitrile is a candidate drug that is able to inhibit URAT1 in transport of uric acid, also significantly increase the amount of uric acid in the body and reduce the toxicity to normal liver cells, so as to prevent or treat hyperuricemia, kidney disease or gout.

At present, 3-bromo-5-(2-ethylimidazo[1,2-α]pyridine-3-carbonyl)-2-hydroxybenzonitrile is still in phase of clinical trials and has not been put into production on a large scale. In the existing process (CN201610810990), 1-Chloromethyl-4-fluoro-1,4-diazoniabicyclo[2.2.2]octane bis(tetrafluoroborate) and iodine are carried out iodination reaction on the benzene ring, then the iodine is cyanated, and the cyanated bromoacetophenone and N-(pyridin-2-yl) propionamide undergoes a ring-closing reaction. In this route, the ring-closing reaction is a heating reaction in a single solvent and thus is not complete, and the conversion rate is not high, resulting in difficult purification and low separation yield, which is not conducive to industrial production.

SUMMARY

One object of the present invention is to provide a method for synthesizing (2-ethylimidazolpyridin-3-yl)(phenyl)methanone compounds in view of the deficiencies in the prior art.

Another object of the present invention is to provide a method for synthesizing 3-bromo-5-(2-ethylimidazo[1,2-α]pyridine-3-carbonyl)-2-hydroxybenzonitrile, the method, with advantages of easy operation, mild conditions and high yield, is thus suitable for industrial production.

The objects of the present invention can be achieved by the following measures:

A method for synthesizing a compound represented by formula (III), comprising step A or step B,

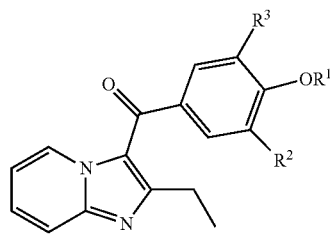

(III)

Step A: a compound represented by formula (I) and a compound represented by formula (II) are first heated in an organic solvent to react, and the resulting reaction product and a base are heated in the presence of water to continue the reaction to obtain a compound represented by formula (III);

Step B: a compound represented by formula (I), a compound represented by formula (II), and a base are heated in an organic solvent to react, and the resulting reaction product is heated in the presence of water to continue the reaction to obtain a compound represented by formula (III);

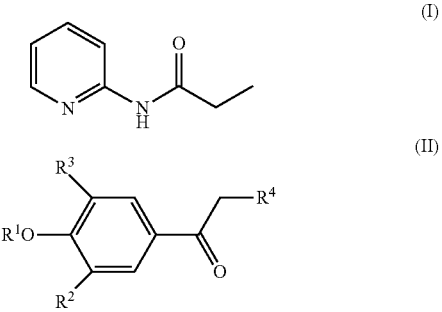

(I)

(II)

wherein, $R^1$ is H or $C_{1-3}$ alkyl, $R^2$ is H, —CN, I or Br, $R^3$ is H, I or Br, and $R^4$ is Cl, Br or I.

The synthesis reaction of the compound represented by formula (III) is divided into two stages. First, two substrates are reacted for a period of time under heating in an organic solvent, and then heated in the presence of water to continue the reaction. A base is added in the first and/or second stage, we found that using this method for adding a base and two-step reaction can greatly promote the conversion of intermediate products generated in the reaction to the target product, reduce and avoid the generation of by-products, and greatly increase the yield of the target product.

In the first stage of step B, a base needs to be added. In the second stage, the base may continue to be added, or no base may be added. Both methods are within the scope of protection of the present application.

In the synthesis for the compound represented by formula (III), the reaction temperature of the compound represented by formula (I) and the compound represented by formula (II) is 75 to 150° C., preferably 77 to 100° C.; the temperature for continuing the reaction is 50 to 100° C., preferably 60 to 100° C.

In the synthesis of the compound represented by formula (III), the organic solvent is selected from the group consisting of toluene, xylene, NMP, ethyl acetate, isopropyl acetate, isopropanol, ethanol, tert-butanol, acetonitrile and DMF, preferably ethyl acetate.

In the synthesis of the compound represented by formula (III), the base is selected from the group consisting of sodium carbonate, potassium carbonate, sodium bicarbonate, potassium bicarbonate, triethylamine, diisopropylethylamine, lithium hydroxide, sodium hydroxide and potassium hydroxide, preferably sodium bicarbonate.

In the synthesis of the compound represented by formula (III), in step A, the base is added to such an amount that the pH value of the reaction solution that continues to react reaches 4-7; in step B, the amount of base added is 0.1 to 2.5 times the moles of the compound represented by formula (II), preferably 0.5 to 2.5 times, more preferably 0.6 to 1.5 times, still more preferably 0.8 to 1.2 times.

The invention also provides three synthetic routes for 3-bromo-5-(2-ethylimidazo[1,2-α]pyridine-3-carbonyl)-2-hydroxybenzonitrile.

Route 1, synthesis of 3-bromo-5-(2-ethylimidazo[1,2-α]pyridine-3-carbonyl)-2-hydroxybenzonitrile includes the following steps:
(1) an acylation reaction between 2-aminopyridine and an acylating reagent is carried out to obtain compound 1;
(2) 4-methoxyacetophenone undergoes two halogenation reactions to obtain compound VI;
(3) compound VI and compound 1 are first heated in an organic solvent to react, and the resulting reaction product and a base are heated in the presence of water to continue the reaction to obtain compound VII; or compound VI, compound 1, and a base are first heated in an organic solvent to react, and the resulting reaction product is heated in the presence of water to continue the reaction to obtain compound VII;
(4) compound VII reacts with cyanide to obtain compound 5;
(5) compound 5 is subjected to a demethylation reaction to obtain compound 6, followed by a bromination reaction to obtain compound 7;

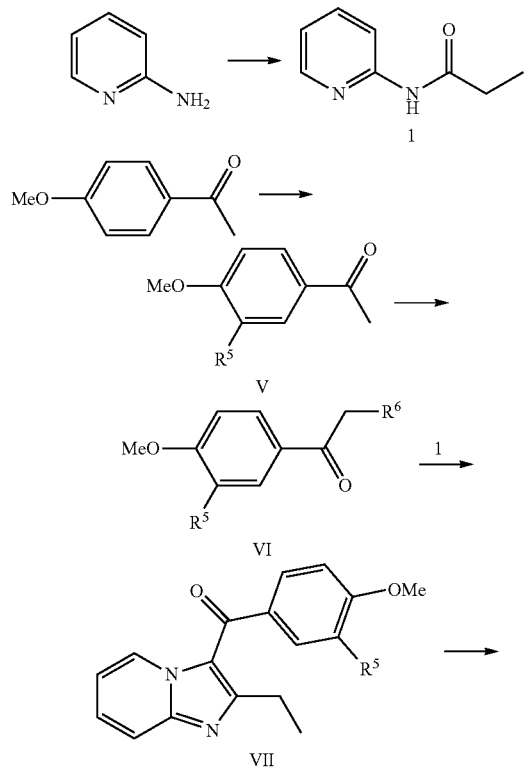

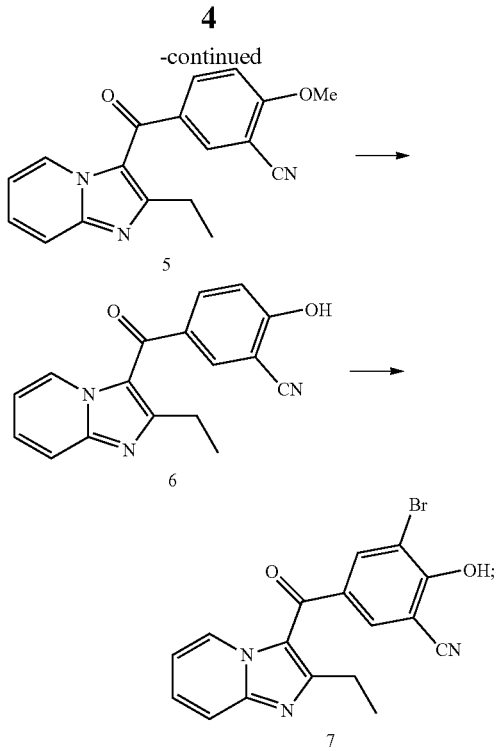

wherein, $R^5$ is I or Br, and $R^6$ is Cl, Br or I.

The following is a detailed description of each step of Route 1.

Step (1): 2-aminopyridine and propionic anhydride undergo an acylation reaction to obtain the corresponding amide (compound 1). Further, 2-aminopyridine and an acylating reagent undergo an acylation reaction under the action of an acid binding agent to obtain compound 1. In this acylation reaction, the acylating reagent can be propionic anhydride or propionyl chloride, and the acid binding agent can be diisopropylethylamine, triethylamine, N-methylpiperidine, potassium carbonate, sodium carbonate and other bases. The reaction solvent may be dichloromethane, THF, acetonitrile, etc. Through experiments, it was found that some diacylated by-products were generated with use of propionyl chloride. With use of propionic anhydride, almost quantitative conversion can be achieved. When triethylamine is used as the acid binding agent in this reaction, the molar ratio of 2-aminopyridine to propionic anhydride can be 1.0:1.0 to 2.0, and the preferred ratio is 1.0:1.1 to 1.4. The reaction temperature is 20 to 45° C. Unlike other steps, there is no specified order between step (1) and step (2) in this method. In specific implementation, step (1) can be performed first to prepare compound 1, or step (2) can be performed first to prepare compound VI, or step (1) and step (2) can be performed simultaneously.

Step (2): 4-methoxyacetophenone undergoes two halogenation reactions to obtain substituted α-haloacetophenone (compound VI). First, under acidic conditions, 4-methoxyacetophenone undergoes a halogenation reaction on the benzene ring, and then the α-position hydrogen atom of the ketone undergoes a substitution reaction to produce α-haloacetophenone. The halogenation in this step is completed in the presence of a halogenating reagent, wherein the halogenating reagent includes a chlorinating reagent, an iodinating reagent and a brominating reagent.

In a preferred embodiment, step (2) is: 4-methoxyacetophenone and an iodinating reagent or brominating reagent undergo a halogenation reaction at 5 to 25° C. under acidic conditions to obtain compound V; a halogenation reaction with a chlorinating reagent, iodinating reagent or brominating reagent is carried out at 5 to 60° C. under acidic conditions or non-acidic conditions to obtain compound VI. When a different reagent is used in the halogenation reaction of the second step, different reaction temperatures can be used, e.g., when an iodinating reagent or brominating reagent is used, the halogenation reaction temperature of the second step can be controlled at 30 to 60° C., when a chlorinating reagent is used, the halogenation reaction temperature can be controlled at 5 to 60° C. In the halogenation reaction of the second step, acidic or non-acidic conditions can be selected according to the conditions.

In step (2), the chlorinating reagent is selected from the group consisting of chlorine, NCS, ammonium chloride, hydrogen chloride and sulfonyl chloride, etc., the iodinating reagent is selected from the group consisting of iodine, NIS, sodium iodide and potassium iodide, and the brominating reagent is selected from the group consisting of NBS, bromine and dibromohydantoin, etc. The reaction solvent is selected from one or more of the group consisting of water, methanol, THF, acetonitrile, acetic acid, propionic acid, and methyl tert-butyl ether; in one embodiment, the solvent is a mixed solvent of water and methanol, or THF, acetonitrile, acetic acid, propionic acid, methyl tert-butyl ether, and their mixed solvents. In the reaction of this step, the solvent for the first halogenation reaction is preferably water, methanol or acetonitrile, or a mixed solvent of two or three of them, and the solvent for the second halogenation reaction is preferably methyl tert-butyl ether, acetic acid, propionic acid, acetone, ethyl acetate or chloroform. The acid in the acidic conditions may be acetic acid, p-toluenesulfonic acid, sulfuric acid, methanesulfonic acid, etc., preferably sulfuric acid, and the brominating reagent is preferably NBS.

There are two-step halogenation reactions in step (2), so the halogenating reagent is added in two stages. It is preferable to add 40 to 85% of the total amount of halogenating agent in the first stage, and add the rest of the halogenating agent in the second stage. Experiments have found that, compared with one-step halogenation reactions using other raw materials, this application, with use of 4-methoxyacetophenone as the raw material for the halogenation reaction and two-step accurately controlled halogenation reactions with different selectivities, can greatly improve the yield of compound VI, inhibit side reactions, and reduce the difficulty of the reaction, so that the preparation process has more industrial application prospects.

Step (3): Compound VI and compound 1 are first heated in an organic solvent to react, and the resulting reaction product and a base are then heated in the presence of water to continue the reaction to obtain compound VII; or compound VI, compound 1 and a base are first heated in an organic solvent to react, and the resulting reaction product is heated in the presence of water to continue the reaction to obtain compound VII. The reaction temperature of compound VI and compound 1 is 75 to 150° C., preferably 77 to 100° C. After compound VI reacts with compound 1, the temperature at which the base is added to continue the reaction is 50 to 100° C., preferably 60 to 100° C. The molar ratio of compound VI to compound 1 is 1:1.0 to 2.0, preferably 1:1.2. In this reaction, the organic solvent is toluene, xylene, NMP, ethyl acetate, isopropyl acetate, isopropanol, ethanol, tert-butanol, acetonitrile, DMF, etc., and preferably ethyl acetate. The base is selected from the group consisting of sodium carbonate, potassium carbonate, sodium bicarbonate, potassium bicarbonate, triethylamine, diisopropylethylamine, lithium hydroxide, sodium hydroxide and potassium hydroxide. In the first case of this step, the base is added to such an amount that the pH value of the reaction solution that continues to react reaches 4-7; in the second case of this step, the amount of base added is 0.1 to 2.5 times the moles of the compound represented by formula (II), preferably 0.5 to 2.5 times, more preferably 0.6 to 1.5 times, still more preferably 0.8 to 1.2 times.

Step (4): The brominated imidazo[1,2-α]pyridine compounds react with cyanide to form benzonitrile compounds (compound 5). The cyanide may be sodium cyanide, potassium cyanide, cuprous cyanide, zinc cyanide, etc., and a mixture thereof, and preferably cuprous cyanide. The reaction solvent is NMP, DMF, DMA, etc., preferably NMP. The reaction temperature is 120 to 200° C., preferably 140 to 160° C.

Step (5): Compound 5 undergoes demethylation and bromination reactions in sequence to obtain 3-bromo-5-(2-ethylimidazo[1,2-α]pyridine-3-carbonyl)-2-hydroxybenzonitrile (compound 7). The demethylation reagent can be BBr$_3$, sodium ethanethiolate, lithium bromide, etc. The bromine source of the bromination reaction is NBS, dibromohydantoin, bromine, etc., the reaction solvent can be acetic acid, DMF, NMP and water, etc. The pH value of the reaction can be in the acidic range or basic range, and the acid can be organic acids such as acetic acid or propionic acid, etc., and the base is inorganic bases such as sodium hydroxide, potassium hydroxide, and lithium hydroxide, etc. Herein, it is preferred to use lithium bromide for a demethylation reaction and then carry out a bromination reaction in water. Compared with other conditions, this can achieve very good reaction and separation effects. The temperature of the demethylation reaction is −50 to 150° C., if BBr3 is used as the demethylation reagent, the reaction temperature is −50 to 20° C., while sodium ethanethiolate or lithium bromide is used as the demethylation reagent, the reaction temperature is 0 to 150° C., preferably 40 to 90° C. The bromine source of the bromination reaction is selected from the group consisting of NBS, dibromohydantoin and bromine, and the temperature of the bromination reaction is 20 to 45° C.; the reaction solvents in the demethylation reaction or the bromination reaction are selected from one or more of the group consisting of dichloromethane, acetic acid, DMF, NMP and water.

Route 2, synthesis of 3-bromo-5-(2-ethylimidazo[1,2-α]pyridine-3-carbonyl)-2-hydroxybenzonitrile includes the following steps:

(1) 4-methoxyacetophenone reacts with an iodinating reagent or brominating reagent to obtain compound IV;

(2) compound IV reacts with cyanide to produce compound 9;

(3) compound 9 is subjected to a halogenation reaction to obtain compound VIII;

(4) compound VIII and compound 1 are first heated in an organic solvent to react, and the resulting reaction product and a base are heated in the presence of water to continue the reaction to obtain compound 5; or compound VIII, compound 1, and base are first heated in an organic solvent to react, and the resulting reaction product is heated in the presence of water to continue the reaction to obtain compound 5;

(5) compound 5 is subjected to a demethylation reaction to obtain compound 6, followed by a bromination reaction to obtain compound 7;

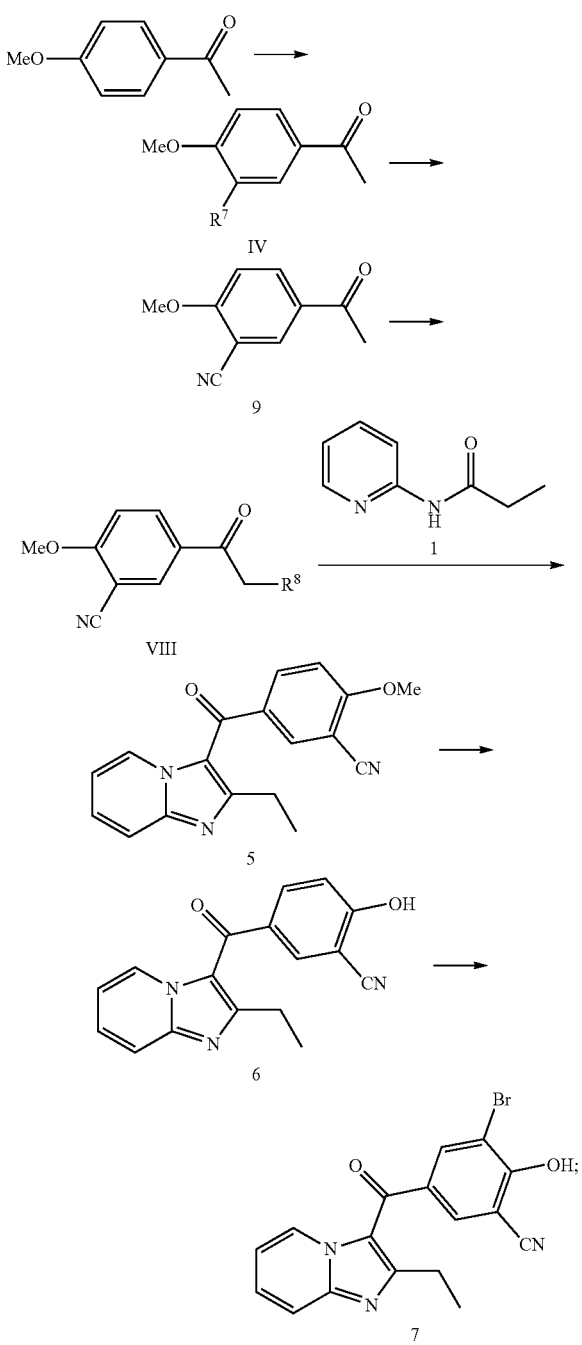

wherein, $R^7$ is I or Br, and $R^8$ is Cl, Br or I.

The following is a detailed description of the steps of Route 2.

In step (1) of Route 2, the iodinating reagent is selected from the group consisting of iodine or NIS, and the brominating reagent is selected from the group consisting of NBS, bromine or dibromohydantoin. The temperature of the iodination or bromination reaction is 5-25° C., and the reaction solvent can be an existing solvent for the iodination or bromination reaction, such as acetonitrile, methanol, etc., and an acid can be appropriately added during the reaction as needed.

In step (2) of Route 2, the cyanide is selected from one or more of the group consisting of sodium cyanide, potassium cyanide, cuprous cyanide and zinc cyanide, preferably cuprous cyanide; the reaction solvent is selected from the group consisting of NMP, DMF and DMA, preferably NMP; the reaction temperature is 120 to 200° C.

In step (3) of Route 2, compound 9 undergoes a halogenation reaction with a halogenating reagent. The halogenating reagent is chlorinating reagents, iodinating reagents or brominating reagents, which are specifically selected from the group consisting of chlorine, NCS, ammonium chloride, hydrogen chloride, sulfonyl chloride, iodine, NIS, sodium iodide, potassium iodide, NBS, bromine and dibromohydantoin. The reaction temperature in this step is 5-25° C., and the reaction solvent can be an existing halogenation solvent, such as acetonitrile, methanol, acetic acid, and propionic acid.

In step (4) of Route 2, the reaction temperature of compound VIII and compound 1 is 75 to 150° C., preferably 77 to 100° C.; the temperature of the continued reaction after the reaction of compound VIII and compound 1 is 50 to 100° C., preferably 60 to 100° C.; the organic solvent is selected from the group consisting of toluene, xylene, NMP, ethyl acetate, isopropyl acetate, isopropanol, ethanol, tert-butanol, acetonitrile and DMF; the base is selected from the group consisting of sodium carbonate, potassium carbonate, sodium bicarbonate, potassium bicarbonate, triethylamine, diisopropylethylamine, lithium hydroxide, sodium hydroxide and potassium hydroxide. In the first case of this step, the amount of base added is such that the pH value of the reaction solution that continues to react reaches 4-7; in the second case of this step, the amount of base added is the mole of the compound represented by formula (II) 0.1 to 2.5 times the amount, preferably 0.5 to 2.5 times, more preferably 0.6 to 1.5 times, still more preferably 0.8 to 1.2 times.

In step (5) of Route 2, a demethylation reagent is used in the demethylation reaction, and the demethylation reagent is selected from the group consisting of BBr3, sodium ethanethiolate and lithium bromide. The temperature of the demethylation reaction is −50 to 150° C., if BBr3 is used as the demethylation reagent, the reaction temperature is −50 to 20° C., and when sodium ethanethiolate or lithium bromide is used as the demethylation reagent, it is The reaction temperature is 0 to 150° C., preferably 40 to 90° C. The bromine source of the bromination reaction is selected from the group consisting of NBS, dibromohydantoin and bromine, and the temperature of the bromination reaction is 20 to 45° C.; the reaction solvent in the demethylation reaction or the bromination reaction is selected from one or more of the group consisting of dichloromethane, acetic acid, DMF, NMP and water.

Route 3, synthesis of 3-bromo-5-(2-ethylimidazo[1,2-α]pyridine-3-carbonyl)-2-hydroxybenzonitrile includes the following steps:

(1) compound 9 is subjected to a demethylation reaction to obtain compound 11;
(2) compound 11 is subjected to a bromination reaction to obtain compound 12, followed by a halogenation reaction to obtain compound IX;
(3) compound IX and compound 1 are first heated in an organic solvent to react, and the resulting reaction product and a base are heated in the presence of water to continue the reaction to obtain compound 7; or compound IX, compound 1, and a base are first heated in an organic solvent to react, and the resulting reaction product is heated in the presence of water to continue the reaction to obtain compound 7;

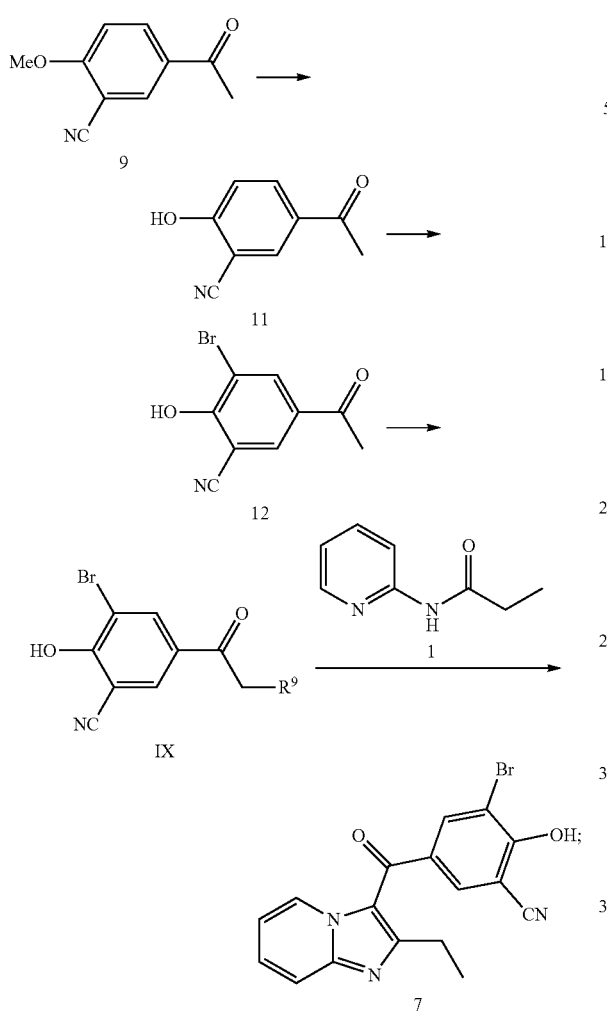

wherein, R⁹ is Cl, Br or I.

The following is a detailed description of the steps of Route 3.

In step (1) of Route 3, the demethylation reagent in the demethylation reaction is selected from the group consisting of BBr3, sodium ethanethiolate and lithium bromide. The temperature of the demethylation reaction is −50 to 150° C., when BBr$_3$ is used as the demethylation reagent, the reaction temperature is −50 to 20° C., and when sodium ethanethiolate or lithium bromide is used as the demethylation reagent, the reaction temperature is 0 to 150° C., preferably 40 to 90° C. The reaction solvent can be dichloromethane, DMF, NMP, etc.

In step (2) of Route 3, the brominating reagent for the bromination reaction is NBS, dibromohydantoin or bromine; preferably, NBS is used in the first bromination reaction, and the bromination reaction temperature is 20 to 45° C.; the solvent is DMF; the second reaction in step (2) is a halogenation reaction, and the halogenating reagent in the reaction includes a chlorinating reagent, an iodinating reagent or a brominating reagent, which is specifically selected from the group consisting of chlorine, NCS, ammonium chloride, hydrogen chloride, sulfonyl chloride, iodine, NIS, sodium iodide, potassium iodide, NBS, bromine and dibromohydantoin, etc. The reaction temperature of the halogenation reaction is 5-25° C., and the reaction solvent can be an existing solvent for halogenation reaction, such as acetonitrile, methanol, acetic acid, propionic acid, chloroform or ethyl acetate, etc.

In step (3) of route 3, the reaction temperature of compound IX and compound 1 is 75 to 150° C., preferably 77 to 100° C.; the temperature of the continued reaction after the reaction of compound IX and compound 1 is 50 to 100° C., preferably 60 to 100° C. The organic solvent is selected from the group consisting of toluene, xylene, NMP, ethyl acetate, isopropyl acetate, isopropanol, ethanol, tert-butanol, acetonitrile and DMF; the base is selected from the group consisting of sodium carbonate, potassium carbonate, sodium bicarbonate, potassium bicarbonate, triethylamine, diisopropylethylamine, lithium hydroxide, sodium hydroxide and potassium hydroxide. In the first case of this step, the base is added to added to such an amount that the pH value of the reaction solution that continues to react reaches 4-7; in the second case of this step, the amount of base added is 0.1 to 2.5 times of the moles of the compound represented by formula (II), preferably 0.5 to 2.5 times, more preferably 0.6 to 1.5 times, still more preferably 0.8 to 1.2 times.

The method of the present invention has the following advantages:

(1) The method for preparing the compound represented by formula (III) is divided into two stages. First, two substrates are reacted for a period of time under heating in an organic solvent, and then heated in the presence of water to continue the reaction. A base is added in the first stage and/or the second stage, use of this method for base addition and two-step reaction can greatly promote the conversion of intermediate products generated in the reaction to the target product, reduce and avoid the generation of by-products, and greatly increase the yield of the target product. Correspondingly, the yield and benefit of other compound synthetic routes using the method for synthesizing the compound represented by the formula (III) of the present invention are also greatly improved;

(2) In the preparation process of compound VI and similar compounds in the present invention, use of two accurately controlled halogenation reactions with different selectivities can greatly increase the yield of the target product, inhibit side reactions, and reduce the difficulty of the reaction, making this preparation process more promising for industrial applications;

(3) The present invention provides a method for preparing the compound represented by formula (III) and multiple routes for preparing compound 7. Each method with mild reaction conditions, simple operation, low equipment requirements, is suitable for laboratory preparation and industrial production;

(4) The reaction product in each step of the present invention is relatively simple in separation and purification, with no need of column chromatography purification, and the separation yield is high;

(5) The raw materials required for the reactions of the present invention can be produced industrially, with low price and easy availability.

DETAILED DESCRIPTION

The present invention will be further described below in reference with examples, but the protection scope of the present invention is not limited to the following examples.

Example 1

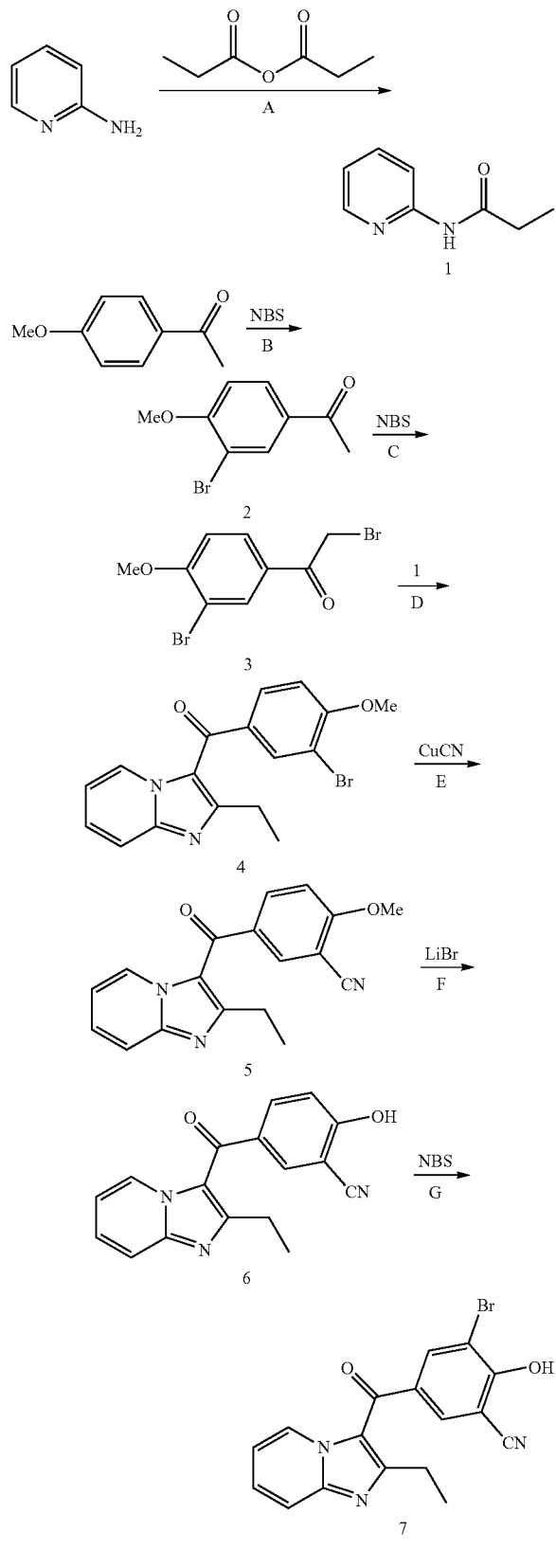

Step A: To a reactor was added dichloromethane (30 L), and then 2-aminopyridine (5.0 kg, 53.1 mol), triethylamine (10.7 kg, 106 mol) and propionic anhydride (8.3 kg, 63.8 mol) were added. After the addition, the resulting mixture was stirred under reflux for 22-24 hours. After the reaction finished, 10% sodium hydroxide solution (25 L) was added at 20 to 25° C. The layers were separated, and the organic layer was washed with water (15 L×2). The combined aqueous layers were extracted with dichloromethane (30 L). The combined organic layers were distilled under reduced pressure to remove most of the solvent, and then recrystallized from n-heptane/dichloromethane to obtain N-(pyridin-2-yl)propionamide (1) (7.7 kg) as a yellow solid, with a HPLC purity of 100% and a yield of 96.6%. $^1$H NMR (DMSO-d6, 300 MHz) δ 10.38 (s, 1H), 8.30-8.28 (m, 1H), 8.11-8.08 (m, 1H), 7.78-7.73 (m, 1H), 7.08-7.04 (m, 1H), 2.39 (q, J=7.5 Hz, 2H), 1.07 (t, J=7.5 Hz, 3H). LCMS: 151.2 [M+H]$^+$.

Step B: To a reactor was added water (27 L) and concentrated sulfuric acid (3 L), and then methanol (35 L), 4-methoxyacetophenone (10 kg, 6.66 mol), and NBS (23.7 kg, 13.3 mol) were added at 10 to 15° C. After the addition, the resulting mixture was stirred at 15-20° C. for 24-28 hours. After the reaction finished, water (40 L) was added. After filtration, the filter cake was washed with water (4 L). The resulting solid was recrystallized from n-heptane to obtain crude 1-(3-bromo-4-methoxyphenyl)ethanone (2) (16.6 kg), which was used directly in the next reaction without purification.

Step C: To a reactor was added methyl tert-butyl ether (82.9 L) and concentrated sulfuric acid (0.71 kg, 7.24 mol), then the crude compound (2) (16.6 kg), and the resulting mixture was stirred under reflux for 2 hours. NBS (7.12 kg, 4.0 mol) was added, and the stirring continued under reflux for 2 to 3 hours. After the reaction finished, the mixture was cooled to 5 to 10° C. After filtration, the filter cake was slurried successively with water (50 L) and 5% sodium thiosulfate solution (50 L), and then recrystallized from n-heptane to obtain 2-bromo-1-(3-bromo-4-methoxyphenyl)ethanone (3) (13.3 kg) as a white solid, with a HPLC purity of 98.7%. The total yield of the two-step reaction of steps B and C was 65.4%. $^1$H NMR (CDCl$_3$, 300 MHz) δ 8.23-8.22 (m, 1H), 8.00-7.96 (m, 1H), 7.00-6.97 (m, 1H), 4.40 (s, 2H), 4.01 (s, 3H). LCMS: 308.9 [M+H]$^+$.

Step D: To a reactor was added ethyl acetate (75 L), compound 1 (4.42 kg, 29.4 mol) and compound 3 (7.50 kg, 24.3 mol). After the addition, the resulting mixture was stirred under reflux for 48-60 hours under nitrogen. After the reaction finished, the mixture was cooled to 20 to 30° C., filtered, and the filter cake was washed with ethyl acetate (7.5 L). Water (75 L) and the resulting solid from the filtration were added to the reactor, the mixture was adjusted to a pH of 4-6 by adding 10% sodium bicarbonate solution dropwise at 90 to 100° C., and then continuously stirred at this temperature for 3 to 5 hours. After the reaction finished, the mixture was cooled to room temperature, and adjusted to a pH of 7-8 with 10% sodium bicarbonate solution. After filtration, the filter cake was washed with water (7.5 L), and then recrystallized from acetonitrile/methyl tert-butyl ether to obtain a white solid (3-bromo-4-methoxyphenyl) (2-ethylimidazo[1, 2-a]pyridin-3-yl)methanone (4) (5.68 kg). The HPLC purity was 99.6%, and the yield was 64.7%. $^1$H NMR (DMSO-d6, 300 MHz) δ 9.18-9.15 (m, 1H), 8.11-8.03 (m, 3H), 7.94-7.82 (m, 1H), 7.64-7.55 (m, 1H), 7.40-7.32 (m, 1H), 3.96 (s, 3H), 2.58 (q, J=7.5 Hz, 2H), 1.23 (t, J=7.5 Hz, 3H). LCMS: 359.1 [M+H]$^+$.

Alternatively, step D: A mixture containing ethyl acetate (45 mL), compound 1 (1.70 g, 11.3 mmol) and compound 3 (2.90 g, 9.42 mmol) was stirred under reflux for 48 hours under nitrogen. After the reaction finished, the mixture was cooled to 20 to 30° C., filtered, and the filter cake was washed with ethyl acetate (15 mL). The filter cake was added to water (30 mL), the temperature was raised to 90 to 100° C., and then the pH value was adjusted to 5 to 6 by adding triethylamine dropwise. After the addition, the resulting mixture was stirred overnight under reflux, and adjusted to a pH of 7 to 8 with 10% sodium bicarbonate solution. The mixture was cooled to room temperature, filtered, and the filter cake was washed with water, and then recrystallized from acetonitrile/methyl tert-butyl ether to obtain (3-bromo-4-methoxyphenyl)(2-ethylimidazo[1,2-a]pyridin-3-yl)methanone (4) (1.68 g), with a yield of 49.6%.

Step E: To a reactor was added NMP (8.1 L), compound 4 (2.70 kg, 7.52 mol) and cuprous cyanide (0.86 kg, 9.60 mol). After the addition, the resulting mixture was stirred at 145 to 155° C. under nitrogen for 24 to 28 hours. After the reaction finished, the mixture was cooled to 85 to 95° C. and 13% ammonia (27 L) was added. Then the mixture was cooled to 15 to 25° C. and continuously stirred for 2 hours. After filtration, the filter cake was washed with 13% ammonia water (2.7 L). The resulting solid was slurried with dichloromethane (13.5 L×2), and the product was in the filtrate. The combined filtrates were washed with 13% ammonia (13.5 L×3). The organic layer was distilled under reduced pressure to remove most of the solvent, and recrystallized from isopropyl acetate/dichloromethane to obtain a yellow solid 5-(2-ethylimidazo[1,2-α]pyridine-3-carbonyl)-2-hydroxybenzonitrile (5) (1.91 kg). The HPLC purity was 98.6%, and the yield was 83.2%.

Step F: To a reactor was added NMP (9.8 L) and compound 5 (1.95 kg, 6.39 mol), and then lithium bromide (1.66 kg, 19.1 mol) and sodium acetate (2.09 kg, 25.5 mol) were added at 75 to 85° C. After the addition, the resulting mixture was stirred at 120 to 130° C. for 10 to 12 hours. After the reaction finished, the mixture was cooled to room temperature, water (29 L) was added, and the pH was adjusted to 5-6 with acetic acid. After filtration, the filter cake was recrystallized from NMP/acetonitrile to obtain 5-(2-ethylimidazo[1,2-α]pyridine-3-carbonyl)-2-hydroxybenzonitrile (6) (1.59 kg) as a yellow solid. The HPLC purity was 99.7%, and the yield was 85.4%. LCMS: 292.0 [M+H]$^+$.

Step G: To a reactor was added water (15.6 L), sodium hydroxide (0.22 kg, 5.5 mol) and compound 6 (1.56 kg, 5.36 mol), and then NBS (0.95 kg, 5.34 mol) was added at 25 to 30° C. After the addition was complete, the resulting mixture was continuously stirred at this temperature for 0.5 to 1.5 hours. After the reaction finished, isopropyl acetate (7.8 L) was added and the pH was adjusted to 5-6 with acetic acid. After filtration, the filter cake was washed with water (3.9 L×2), and then recrystallized from DMSO/isopropyl acetate to obtain 3-bromo-5-(2-ethylimidazo[1,2-α]pyridine-3-carbonyl)-2-hydroxybenzonitrile (7) (1.59 kg) as a yellow solid. The HPLC purity was 99.9%, and the yield was 80.1%. $^1$H NMR (DMSO-d6, 300 MHz) δ 9.13-9.11 (m, 1H), 8.12-8.11 (m, 1H), 8.03-7.97 (m, 1H), 7.86-7.83 (m, 1H), 7.77-7.72 (m, 1H), 7.34-7.29 (m, 1H), 2.57-2.50 (m, 2H), 1.19 (t, J=7.5 Hz, 3H). LCMS: 370.0 [M+H]$^+$.

Example 2

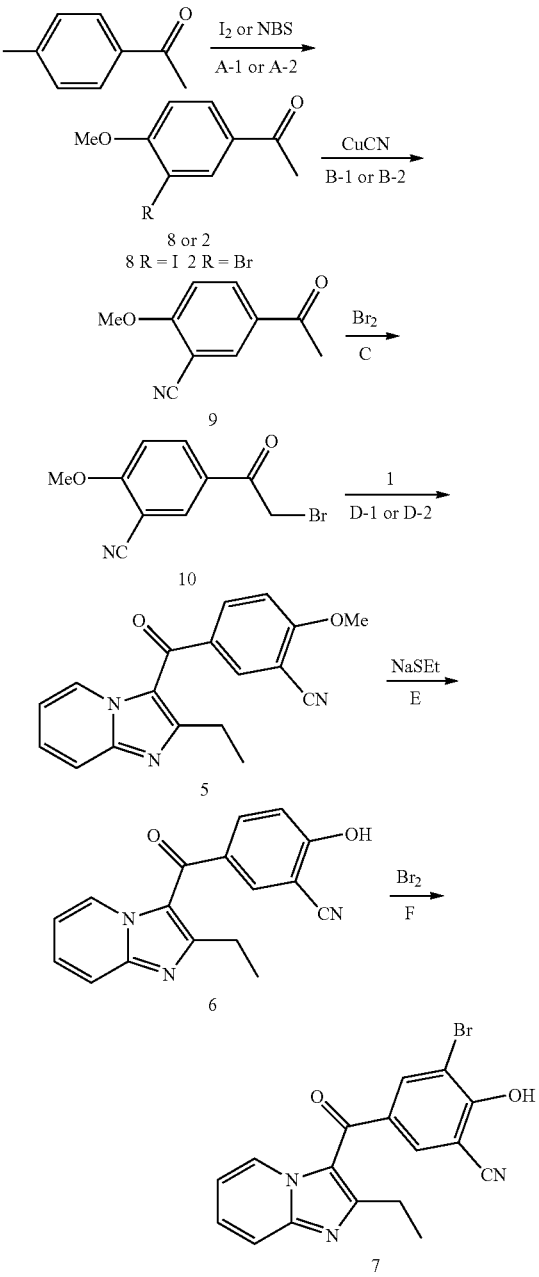

Step A-1: To a solution of 4-methoxyacetophenone (600 g, 4.0 mol) in acetonitrile (5.4 L) was added iodine (518 g, 2.04 mol) and 1-chloromethyl-4-fluoro-1,4-diazabicyclo[2.2.2]octane bis(tetrafluoroborate) (1.42 kg, 4.0 mol). After the addition, the resulting mixture was stirred at 12 to 20° C. for 20 hours. After the reaction finished, water (24 L) was added, the mixture was stirred for 15 minutes, and filtered. The filter cake was washed successively with 5% sodium thiosulfate solution (1.5 L) and water (3.0 L). After drying, 3-iodo-4-methoxyacetophenone (8) (894 g) was obtained as a yellow solid. The yield was 81.0%.

The experimental operation of step A-2 is the same as that of step B in Example 1, and 1-(3-bromo-4-methoxyphenyl)ethanone (2) was obtained.

Step B-1: To a solution of compound 8 (467 g, 1.69 mol) in DMF (2.0 L) was added cuprous cyanide (228 g, 2.55 mol). After the addition, the resulting mixture was stirred at 110 to 120° C. under nitrogen overnight. After cooling to room temperature, dichloromethane (5.0 L) was added. The mixture was stirred for 15 minutes, filtered through celite, and the filter cake was washed with an appropriate amount of dichloromethane. Water (7.0 L) was added, the layers were separated, and the aqueous layer was extracted with dichloromethane (5.0 L). The combined organic layers were washed sequentially with water (3.0 L×3) and saturated brine (2.0 L). The solvent was evaporated under reduced pressure, and the resulting product was slurried with petroleum ether (500 mL) to obtain 5-acetyl-2-methoxybenzonitrile (9) (263 g) as a yellow solid. The yield was 88.8%.

Step B-2: To a solution of compound 2 (56.0 g, 244 mmol) in NMP (300 mL) was added cuprous cyanide (32.8 g, 366 mol). After the addition, the resulting mixture was stirred at 150 to 160° C. under nitrogen overnight. After cooling to room temperature, dichloromethane (850 mL) was added. The mixture was stirred for 15 minutes, filtered through celite, and then the filter cake was washed with an appropriate amount of dichloromethane. Water (1.2 L) was added, the layers were separated, and the aqueous layer was extracted with dichloromethane (400 mL×2). The combined organic layers were washed sequentially with water (250 mL×3) and saturated brine (200 mL). The solvent was evaporated under reduced pressure, and the resulting product was slurried with petroleum ether (110 mL) to obtain 5-acetyl-2-methoxybenzonitrile (9) (29.1 g) as a yellow solid. The yield was 68.1%.

Step C: Bromine (422 g, 2.64 mol) was added dropwise to a mixture containing compound 9 (385 g, 2.20 mol) and methanol (2.9 L) at 7 to 15° C. After the addition, the resulting mixture was stirred at 20° C. overnight. After the reaction finished, the mixture was filtered, and the filter cake was dissolved with dichloromethane (4.0 L), and then washed with saturated brine (1.3 L×2). The solvent was evaporated under reduced pressure, and the resulting product was slurried with petroleum ether (400 mL) to obtain 5-(2-bromo-acetyl)-2-hydroxy-3-methylbenzonitrile (10) (458 g) as a white solid. The yield was 81.9%.

Step D-1: A mixture containing compound 1 (118 g, 785 mmol), compound 10 (200 g, 787 mmol) and ethyl acetate (2.5 L) was stirred under reflux for 48 hours under nitrogen. The mixture was cooled to room temperature, filtered, and the filter cake was washed with ethyl acetate (500 mL). To the solid was added water (3 L), and the resulting mixture was heated to 90 to 100° C., adjusted to a pH of 5 to 6 by adding 10% sodium bicarbonate solution dropwise, and continuously stirred at this temperature for 3 hours. After the reaction finished, the mixture was cooled to room temperature, and adjusted to a pH of 7-8 with 10% sodium bicarbonate solution. After filtration, the filter cake was recrystallized from ethanol to obtain 5-(2-ethylimidazo[1,2-α]pyridine-3-carbonyl)-2-hydroxybenzonitrile (5) (160 g) as a pale yellow solid. The yield was 69.5%. $^1$H NMR (DMSO-d6, 400 MHz) δ 9.27-9.25 (m, 1H), 8.10 (d, J=2.4 Hz, 1H), 8.02 (dd, J=2.4, 8.8 Hz, 1H), 7.79-7.76 (m, 1H), 7.64-7.60 (m, 1H), 7.42 (d, J=8.8 Hz, 1H), 7.23-7.20 (m, 1H), 4.03 (s, 3H), 2.39 (q, J=7.6 Hz, 2H), 1.26 (t, J=7.6 Hz, 3H). LCMS: 306.0 [M+H]$^+$.

Step D-2: A mixture containing compound 1 (8.87 g, 59.1 mmol), compound 10 (15.0 g, 59.0 mmol), sodium bicarbonate (4.96 g, 59.0 mmol) and ethyl acetate (200 mL) were stirred under reflux for 48 hours under nitrogen. The solvent was evaporated under reduced pressure, and then ethanol (10 mL) was added. The mixture was stirred for 10 minutes, and filtered. The resulting mixture of solid and water (225 mL) was stirred at 90 to 100° C. for 3 hours. After the reaction finished, the mixture was cooled to room temperature, and adjusted to a pH of 7-8 with 10% sodium bicarbonate solution. After filtration, the filter cake was recrystallized from ethanol to obtain 5-(2-ethylimidazo[1,2-α]pyridine-3-carbonyl)-2-hydroxybenzonitrile (5) (11.1 g) as a pale yellow solid. The yield was 64.2%.

Step E: Sodium ethanethiolate (39.9 g, 467 mmol) was added to a solution of compound 5 (70.0 g, 239 mmol) in DMF (350 mL). After the addition, the resulting mixture was stirred at 48-55° C. for 0.5 hours. After the reaction finished, the mixture was cooled to room temperature and poured into water (1.05 L). Insolubles were removed by filtration. The pH value of the filtrate was adjusted to 5-6 with 10% citric acid solution. After filtration, the filter cake was washed with an appropriate amount of water, and the resulting solid was recrystallized from acetonitrile to obtain 5-(2-ethylimidazo[1,2-α]pyridine-3-carbonyl)-2-hydroxybenzonitrile (6) (59.0 g). The yield was 88.3%.

Step F: Bromine (36.6 g, 229 mmol) was added dropwise to a mixture containing compound 6 (58.0 g, 199 mmol), sodium acetate (33.0 g, 402 mmol) and acetic acid (580 mL) at 15-20° C. After the addition, the resulting mixture was continuously stirred at this temperature for 2 hours. The above reaction solution was poured into water (580 mL). After filtration, the resulting solid was suspended in water (600 mL), and adjusted to a pH of 5-6 with 2 M sodium hydroxide solution. After filtration, the resulting solid was washed with water (120 mL), and then recrystallized from DMSO/isopropyl acetate to obtain 3-bromo-5-(2-ethylimidazo[1,2-α] pyridine-3-carbonyl)-2-hydroxybenzonitrile (7) (63.7 g) as a yellow solid. The yield was 86.5%. $^1$H NMR and MS of Compound 7 are consistent with those in Example 1.

Example 3

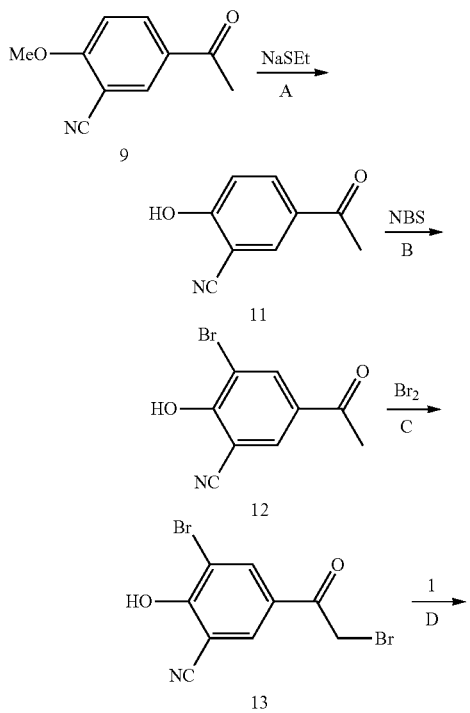

-continued

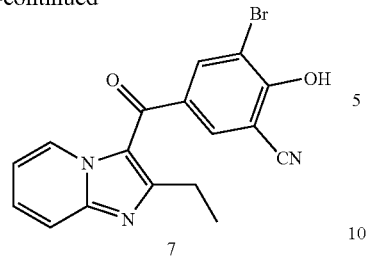

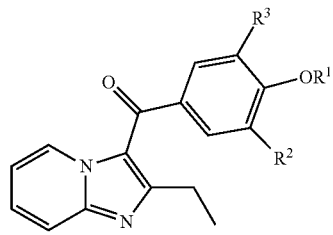

Step A: A mixture containing compound 9 (50.0 g, 285 mmol), sodium ethanethiolate (28.8 g, 342 mmol) and DMF (200 mL) was stirred at 70 to 80° C. for 1 hour. After cooling to room temperature, water (700 mL) was added, and insolubles were removed by filtration. The filtrate was extracted with ethyl acetate (100 mL), and the product was in the aqueous phase. The aqueous phase was adjusted to a pH of 5-6 with 10% citric acid solution, and extracted with ethyl acetate (200 mL×3). The combined organic phase was washed successively with water (100 mL×2) and saturated brine (100 mL), and the solvent was evaporated under reduced pressure. The resulting product was recrystallized from petroleum ether/ethyl acetate to obtain 5-acetyl-2-hydroxylbenzoonitrile (11) (42.3 g). The yield was 92.1%.

Step B: NBS (36.8 g, 207 mmol) was added to a solution of compound 11 (30.3 g, 188 mmol) in DMF (150 mL) in batches. After the addition, the resulting mixture was stirred at room temperature for 1.5 hours. Water (530 mL) was added and the mixture was extracted with ethyl acetate (150 mL×3). The combined organic phase was washed successively with water (90 mL×2) and saturated brine (45 mL), and the solvent was evaporated under reduced pressure. The resulting product was recrystallized from petroleum ether/ethyl acetate to obtain 5-acetyl-3-bromo-2-hydroxybenzonitrile (12) (39.0 g). The yield was 86.4%.

Step C: Bromine (16.7 g, 104 mmol) was added dropwise to a solution of compound 12 (24.0 g, 100 mmol) in chloroform (360 mL). After the addition, the resulting mixture was stirred at 10 to 15° C. overnight. After the reaction, the mixture was washed successively with 5% sodium thiosulfate solution (50 mL) and saturated brine (90 mL). The solvent was evaporated under reduced pressure to obtain 3-bromo-5-(2-bromoacetyl)-2-hydroxybenzonitrile (13) (29.7 g). The yield was 93.1%.

Step D: A mixture containing compound 1 (9.66 g, 64.3 mmol), compound 13 (20.5 g, 64.3 mmol) and ethyl acetate (300 mL) was stirred under reflux for 48 hours under nitrogen. The mixture was cooled to room temperature, filtered, and the filter cake was washed with ethyl acetate (40 mL). The resulting mixture of solid and water (300 mL) was heated to 60 to 70° C., adjusted to a pH of 5 to 6 by adding 10% sodium bicarbonate solution dropwise, and then the temperature was raised to reflux and kept at this temperature for 3 hours. After the reaction finished, the mixture was cooled to room temperature, and adjusted to a pH of 7-8 with 10% sodium bicarbonate solution. After filtration, the filter cake was recrystallized from DMSO/isopropyl acetate to obtain 3-bromo-5-(2-ethylimidazo[1,2-α]pyridine-3-carbonyl)-2-hydroxybenzonitrile as a yellow solid (7) (10.5 g). The yield was 45.7%. $^1$H NMR and MS of compound 7 are consistent with those in Example 1.

What is claimed is:

1. A method for synthesizing a compound represented by formula (III), comprising step A or step B, Step A: a compound represented by formula (I) and a compound represented by formula (II) are first heated in an organic solvent to react, and the resulting reaction product and a base are heated in the presence of water to continue the reaction to obtain a compound represented by formula (III);

Step B: a compound represented by formula (I), a compound represented by formula (II), and the base are heated in an organic solvent to react, and the resulting reaction product is heated in the presence of water to continue the reaction to obtain a compound represented by formula (III);

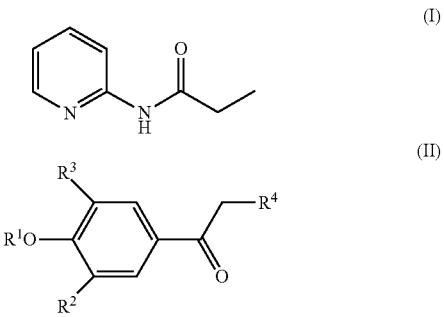

wherein, $R^1$ is H or C1-3 alkyl, $R^2$ is H, —CN, I or Br, $R^3$ is H, I or Br, and $R^4$ is Cl, Br or I; the organic solvent is selected from the group consisting of toluene, xylene, ethyl acetate, isopropyl acetate, isopropanol, ethanol, N-methyl-2-pyrrolidone (NMP), tert-butanol, dimethylformamide (DMF) and acetonitrile;

wherein the base is selected from the group consisting of sodium carbonate, potassium carbonate, sodium bicarbonate, potassium bicarbonate, triethylamine, diisopropylethylamine, lithium hydroxide, sodium hydroxide and potassium hydroxide.

2. The method according to claim 1, wherein the reaction temperature of the compound represented by formula (I) and the compound represented by formula (II) is 75 to 150° C. the temperature for continuing the reaction is 50 to 100° C.

3. The method according to claim 1, wherein the organic solvent is ethyl acetate.

4. The method according to claim 1, wherein in step A, the base is added to such an amount that the pH value of the reaction solution that continues to react reaches 4 to 7; in step B, the amount of the base added is 0.1 to 2.5 times the moles of the compound represented by formula (II).

5. The method according to claim 2, wherein the reaction temperature of the compound represented by formula (I) and the compound represented by formula (II) is 77 to 100° C.; the temperature for continuing the reaction is 60 to 100° C.

6. The method according to claim 4, wherein the base is sodium bicarbonate; in step B, the amount of the base added is 0.5 to 2.5 times the moles of the compound represented by formula (II).

* * * * *